(12) United States Patent
Diaz-Quijada et al.

(10) Patent No.: US 8,057,852 B2
(45) Date of Patent: Nov. 15, 2011

(54) MICRODEVICE FOR A FLUORESCENCE-BASED ASSAY, AND A METHOD FOR MAKING THE MICRODEVICE

(75) Inventors: Gerardo A. Diaz-Quijada, Montreal (CA); Teodor Veres, Montreal (CA)

(73) Assignee: National Research Council of Canada, Ottawa, ON (CA)

( * ) Notice: Subject to any disclaimer, the term of this patent is extended or adjusted under 35 U.S.C. 154(b) by 1295 days.

(21) Appl. No.: 11/563,011

(22) Filed: Nov. 23, 2006

(65) Prior Publication Data
US 2008/0124246 A1    May 29, 2008

(51) Int. Cl.
*B05D 5/06*    (2006.01)
(52) U.S. Cl. ........ 427/164; 427/162; 422/547; 422/552; 422/553
(58) Field of Classification Search ............ 422/102, 422/82.08, 552, 553, 547; 435/288.3, 288.4, 435/288.5; 156/272.2, 272.6, 273.1, 273.3, 156/273.5; 427/162, 164
See application file for complete search history.

(56) References Cited

U.S. PATENT DOCUMENTS

| 4,687,808 | A * | 8/1987 | Jarrett et al. ............... 525/54.1 |
| 5,728,420 | A * | 3/1998 | Keogh ........................ 427/2.12 |
| 5,811,185 | A | 9/1998 | Schreck et al. |
| 6,171,780 | B1 * | 1/2001 | Pham et al. ..................... 435/4 |
| 6,548,121 | B1 | 4/2003 | Misev et al. |
| 2002/0092767 | A1 * | 7/2002 | Bjornson et al. ............. 204/451 |
| 2004/0214127 | A1 | 10/2004 | Kubo et al. |
| 2008/0248589 | A1 * | 10/2008 | Belisle et al. ................ 436/518 |

FOREIGN PATENT DOCUMENTS

| DE | 44 26 398 | 2/1996 |
| DE | 44 26 399 | 2/1996 |
| EP | 0 694 568 | 7/1994 |
| EP | 0 694 567 | 7/1995 |

(Continued)

OTHER PUBLICATIONS

Atomic Force Microscopy—Tone Reversal of an AFM Lateral Force Image Due to Hybridization of Oligonucleotides Immobolized On Polymers—2005 Wiley-VCH Verlag GmbH & Co.No. 6, 610-613.

(Continued)

*Primary Examiner* — Jill Warden
*Assistant Examiner* — Dwayne K Handy
(74) *Attorney, Agent, or Firm* — Marks & Clerk; Richard J. Mitchell

(57) ABSTRACT

Glass as a substrate for fluorescence-based assays is expensive. Disclosed is a poly(cyclic olefin) alternative to glass that is of comparable sensitivity. More specifically, disclosed is a method of making a microdevice for the immobilization of biomolecules for the purpose of carrying out a fluorescence-based assay, said method comprising providing a substrate comprising a poly(cyclic olefin); protecting the substrate from ultraviolet (UV) light; and subjecting a surface of said UV-protected substrate to ozone oxidation to activate said surface; wherein a content of intrinsic fluorophores on the surface of the substrate remains substantially unchanged after the ozone oxidation. Also disclosed is a microdevice for the immobilization of biomolecules for the purpose of carrying out a fluorescence-based assay, said microdevice comprising a body comprising a poly(cyclic olefin), said body having an ozone-activated surface substantially free of intrinsic fluorophores; wherein said activated surface is substantially free of intrinsic fluorescence during a fluorescence-based assay of said biomolecules bound to said activated surface.

15 Claims, 3 Drawing Sheets

FOREIGN PATENT DOCUMENTS

| | | |
|---|---|---|
| FR | 2 872 911 | 7/2004 |
| JP | 2001231556 | 8/2001 |
| JP | 2004081837 | 3/2004 |
| WO | WO 02/18634 | 3/2002 |
| WO | WO 2004/056496 | 7/2004 |
| WO | WO 2005/122352 | 12/2005 |
| WO | WO 2006/005887 | 1/2006 |
| WO | WO 2006-067061 | 6/2006 |

OTHER PUBLICATIONS

Study on Protein (IgG) Adsorption in Terms of Surface Modification of Cyclic Olefin Copolymer (COC) for Protein Biochip—Y. Baba et al Micro Total Analysis Ststems 2002, vol. 1, 419-421.

Surface Modification of Cyclic Olefinic Copolymers for Bio-MEMS Microfluidic Devices—C.Ahn, S. Kim, H.Chao, S.Murugesan Mat. Res.Soc. Sump.Proc. vol. 729 2002 Materials ResearchSociety.

Advanced Functional Materials—Surface Functionalization of Thermoplastic Polymers for the Fabrication of Microfluidic Devices by Photoinitiated Grafting—2003 Wiley-VCH Verlag GmbH & Co. 2003, 13, No. 4 April.

Protein Array Patterning on Cyclic Olefin Copolymer (COC) for Disposable Protein Chip—2004 American Scientific Publishers—Sensor Lett. vol. 2 No. 3, 4, 2004.

Surface Studies of Low Molecular Weight Photolysis Products from UV-ozone Oxidised Polystyrene—M.R.Davidson, S.A.Mitchell, R.H.Bradley Advanced Materials and Biomaterials Research Centre, Mar. 17, 2005.

* cited by examiner

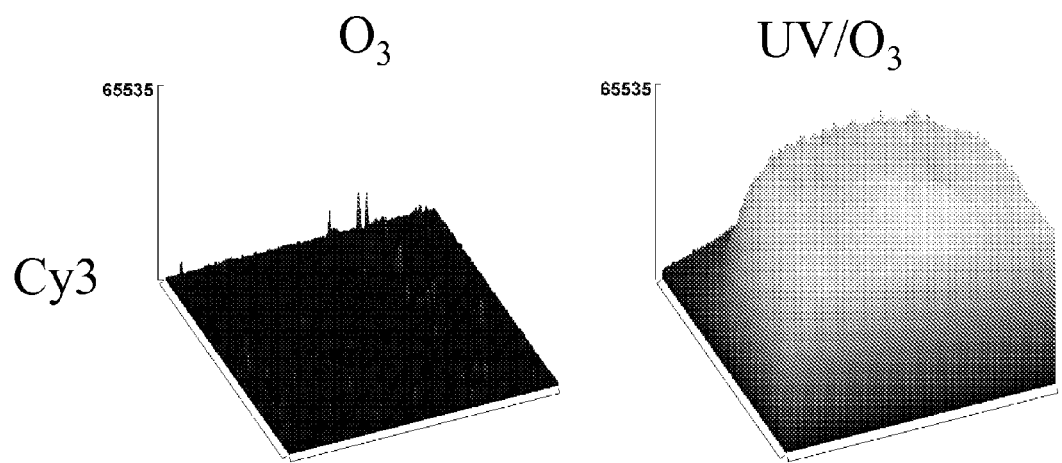
Fig. 1a
Fig. 1b
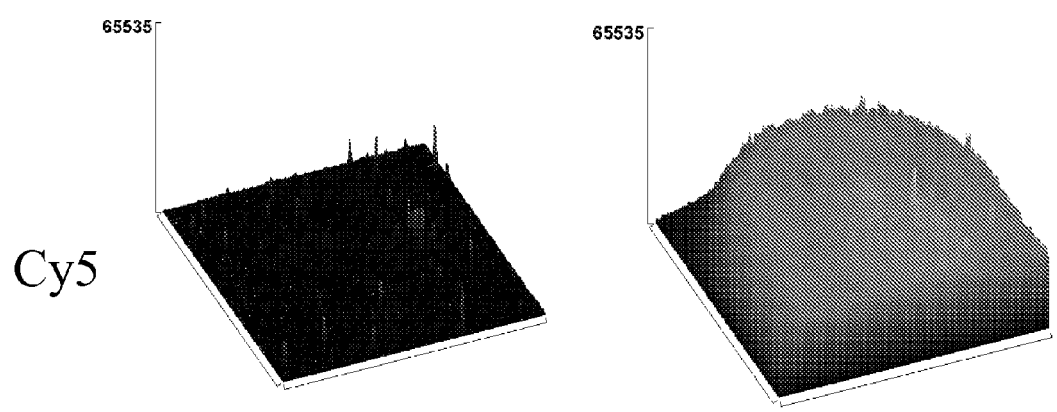
Fig. 1c
Fig. 1d

MICRODEVICE FOR A FLUORESCENCE-BASED ASSAY, AND A METHOD FOR MAKING THE MICRODEVICE

BACKGROUND OF THE INVENTION

1. Field of the Invention

The present invention relates to the use of ozone in the activation of the surface of a poly(cyclic olefin) substrate in the absence of UV light, for the production of a substrate suitable for a fluorescence-based assay.

2. Background Art

High throughput technologies, particularly microarrays, have had a large impact in life sciences. Microarrays not only permit carrying out a large number of experiments in a parallel format, but also decrease significantly the amounts of reagents required for the analysis. Traditionally, glass has been the substrate of choice for the fabrications of microarrays and this is partly due to the existence of rather simple and well-known surface modification methods that are based on silane chemistry.

The main problem with the use of glass is expense. Chemically modified glass slides for microarray technologies are expensive and therefore plastic slides are an economical alternative. Moreover, micromachining of glass is an extremely expensive process and as a consequence this material is not suitable for 1) enhancing microarray slides with micro/nano-structures which would increase the surface area and therefore enhance the detection limit and 2) fabrication of nano/microfluidic-based systems for high throughput screening devices.

Several approaches are presented in the literature for the chemical modification of a poly(cyclic olefin) substrate. For instance, plasma treatment has been employed successfully to increase the hydrophilicity of the plastics (J. Kai, Y.-S. Sohn, C. H. Ahn, Micro Total Analysis Systems 2002, Proceedings of the mTAS 2002 Symposium, 6th, Nara, Japan, Nov. 3-7, 2002 2002, 1, 419-421; Y.-S. Sohn, J. Kai, C. H. Ahn, Sens. Lett. 2004, 2, 3, 4, 171-174; D. Nikolova, E. Dayss, G. Leps, A. Wutzler, Surf. Interface Anal. 2004, 36, 8, 689-693; A. Puntambekar, S. Murugesan, R. Trichur, H. J. Cho, S. Kim, J.-W. Choi, G. Beaucage, C. H. Ahn, Micro Total Analysis Systems 2002, Proceedings of the mTAS 2002 Symposium, 6th, Nara, Japan, Nov. 3-7, 2002 2002, 1, 425-427; C. Ahn, S. Kim, H. Chao, S. Murugesan, G. Beaucage, Materials Research Society Symposium Proceedings 2002, 729, BioMEMS and Bionanotechnology, 131-136). This is an aggressive method that generates a large number of polar groups such as hydroxyl groups. However, this technique is difficult to implement on an industrial scale since it requires expensive high vacuum systems.

A second approach involves reacting the poly(cyclic olefin) surface with highly reactive intermediates (H. J. Mathieu, Y. Chevolot, L. Ruiz-Talor, D. Leonard, Adv. Polym. Sci. 2003, 162, 1-34; J. J. Tate, J. Persinger, B. Bartholomew, Nucleic Acids Res. 1998, 26, 6, 1421-1426), such as free radicals (T. Rohr, D. F. Ogletree, F. Svec, J. M. J. Frechet, Adv. Funct. Mater. 2003, 13, 4, 264-270), nitrenes (K. A. Schnapp, R. Poe, E. Leyva, N. Soundararajan, M. S. Platz, Bioconjug. Chem. 1993, 4, 172-177; K. A. Schnapp, M. S. Platz, Bioconjug. Chem. 1993, 4, 178-183; J. F. W. Keana, S. X. Cai, J. Org. Chem. 1990, 55, 3640-3647) or carbenes (W. Kramer, S. Schneider, J. Lipid Res. 1989, 30, 1281-1288; K. Bergmann, K. E. Carlson, J. A. Katzenellenbongen, Bioconjug. Chem. 1994, 5, 141-150; A. Collioud, J.-F. Clemence, M. Sanger, H. Sigrist, Bioconjug. Chem. 1993, 4, 528-536). Although several degrees of success have been achieved with this approach, some of the precursors for the reactive intermediates are expensive (e.g., fluorinated aryl azides). Moreover, this approach results in many cases in inhomogenous surfaces that are not useful for assay applications (L. M. Shamansky, C. B. Davis, J. K. Stuart, W. G. Kuhr, Talanta 2001, 55, 909-918).

Ozone treatment of poly(cyclic olefins) has been used with respect to preparing a surface for adhesion to other materials on a macroscopic scale. EP 694,567 A2 and EP 694,568 A2 disclose ozone treatment of poly(cyclic olefins) with a view to producing a material that has good adherence properties to metal, glass or plastic. The ozone is preferably produced with a UV source, consistent with aggressive oxidation suitable for that application. US Patent Application 20050181531, filed Jan. 26, 2005, discloses use of ozone-treated poly(cyclic olefin) to improve adhesiveness of a base layer in coating with a bright decoration layer for use in a radar apparatus. Again, the surface of the poly(cyclic olefin) was aggressively treated with plasma ion etching and/or highly concentrated ozone water with a view to subsequent macroscopic modifications.

SUMMARY OF THE INVENTION

In one aspect, the present invention provides a method of making a microdevice for the immobilization of biomolecules for the purpose of carrying out a fluorescence-based assay, said method comprising:

providing a substrate comprising a poly(cyclic olefin);
protecting the substrate from ultraviolet (UV) light; and
subjecting a surface of said UV-protected substrate to ozone oxidation to activate said surface;
wherein a content of intrinsic fluorophores on the surface of the substrate remains substantially unchanged after the ozone oxidation.

In another aspect, the present invention provides a microdevice for the immobilization of biomolecules for the purpose of carrying out a fluorescence-based assay, said microdevice comprising:

a body comprising a poly(cyclic olefin), said body having an ozone-activated surface substantially free of intrinsic fluorophores;
wherein said activated surface is substantially free of intrinsic fluorescence during a fluorescence-based assay of said biomolecules bound to said activated surface.

In another aspect, the present invention provides a microdevice prepared in accordance with the method of the invention.

In carrying out the ozone treatment of poly(olefin) substrate while protecting the substrate from UV light, the generation of intrinsic fluorophores is avoided, these intrinsic fluorophores typically being conjugated unsaturated surface groups created when the surface side groups of the poly (cyclic olefin) are oxidized with ozone and UV.

BRIEF DESCRIPTION OF THE DRAWINGS

FIGS. 1a to 1d show a comparison of the effect of UV (1b and 1d) during ozone treatment of a poly(cyclic olefin) substrate on the intrinsic fluorescence from that substrate. The absence of UV (1a and 1c) results in a significantly lower intrinsic fluorescence.

DESCRIPTION OF THE PREFERRED EMBODIMENTS

Figure 2:
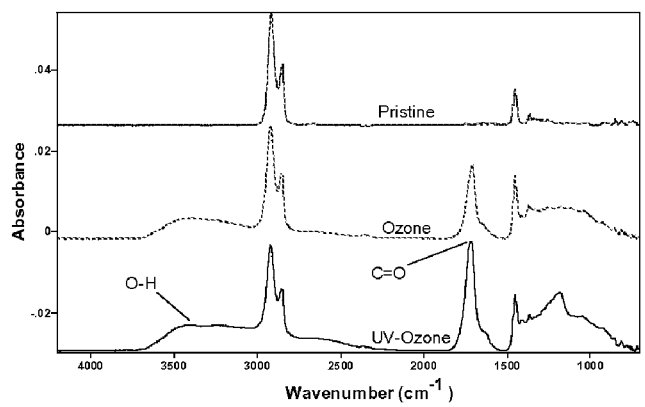
FIG. 2 shows the infrared spectra of untreated, ozone-treated and ozone/UV-treated poly(cyclic olefin).

A microdevice can be any substrate surface on which a fluorescence-based assay is performed, such as a slide for a microarrayer, a microfluidic channel of a microfluidic assay system, a multi-well assay plate, and the like. The substrate surface can include micro- or nanostructures, such as posts, cavities, wells, and the like. The microdevice can be designed for small volume assays, for example in the picoliter scale, or higher volume assays in the micro- to milliliter scales.

The term "activated surface" means a surface having pendant polar groups such as carboxylic acids, aldehydes, ketones, alcohols, esters, acetals, and the like. Any polar group formed by ozone oxidation of the surface of a poly(cylcic olefin) is considered to be part of the "activated surface".

The term "substantially free", in the context of "intrinsic fluorescence" and "intrinsic fluorophores", means the amount of fluorescence emitted from the activated surface of the poly(cyclic olefin) substrate ("inrinsic fluorescence") is negligible and does not interfere with fluorescence emitted from bound assay substances in the emission wavelengths of interest in a fluorescence-based assay.

The term "intrinsic fluorophore" means a group that forms part of the poly(cyclic olefin) substrate, either before or after ozone treatment, and that fluoresces upon excitation with light of a wavelength typically used in fluorescence-based assays. Intrinsic fluorophores produce "intrinsic fluorescence". The term "substantially unchanged" means that any change in a content of intrinsic fluorophores in the poly(cyclic olefin) after ozone oxidation is negligible, and that the level of intrinsic fluorescence from an ozone-treated substrate is effectively the same as the level of intrinsic fluorescence from an untreated substrate with respect to the sensitivity required for fluorescence-based assays.

While an assay substance such as a protein could be bound directly to the activated surface through reaction, for example between amine groups on the protein and pendant carboxylic acid groups on the activated sufface, the use of a reagent to modify pendant groups is also contemplated. The pendant groups can be carboxylic acids, aldehydes, ketones, alcohols, and the like. In one embodiment, pendant carboxlic acid groups on the activated surface of the poly(cyclic olefin) can be modified with N-hydroxysuccinimide (NHS) in the presence of 1-ethyl-3-(3-dimethylaminopropyl)carbodiimide (EDC). Other reagents that conveniently modify carboxylic acid groups can also be used, such as N,N'-carbonyldiimidazole, N-ethyl-3-phenylisoxazolium-3'-sulfonate, diisopropyl carbodiimide, oxalyl chloride, adipic acid dihydrazide, or 1,6-diaminohexane alone (under acid or base catalysis), or followed by treatment with either gluteraldehyde and sodium cyanoborohydride (NaCNBH3) or 2-iminothiolane. Subsequent covalent attachment of biomolecules to the modified activated surface can then be carried out. In the above example, the bound succinimide ester can be reacted with an amine on a biomolecule. The production of free amine, aldehyde, hydrazide or sulfhydryl groups is contemplated, by use of reagents such as those mentioned above, in order to subsequently attach biomolecules by covalent reaction for use in a fluorescence-based assay. Other chemical strategies for the attachment of biomolecules can be envisioned by a person skilled in the art.

Biomolecules can be, but are not limited to, DNA, RNA, oligonucleotides, proteins, such as antibodies, enzymes, etc., peptides, carbohydrates, or any other organic, metallo-organic or inorganic molecules that have biological activity or potential biological activity.

Poly(cyclic olefins) that can be used in the present invention conveniently include a repeating unit that has a saturated hydrocarbon, such as as an alicyclic, structure. Examples of the alicyclic structure include a cycloalkane structure, a cycloalkene structure, and the like. Preferably, the alicyclic structure is the cycloalkane structure. The number of carbon atoms that constitute the alicyclic structure is 4 to 30, preferably 5 to 20, and further preferably 5 to 15. Examples of monomers used for materials for the poly(cyclic olefin) include norbornene, cyclohexene, vinylcyclohexane, and the like.

More specifically, norbornene and derivatives thereof can include 5-methyl-2-norbornene, 5,6-dimethyl-2-norbornene, 5-ethyl-2-norbornene, 5-butyl-2-norbornene, 5-ethylidene-2-norbornene, dicyclopentadiene, 2-3-dihydrodicyclopentadiene, alkyl derivatives thereof such as methyl, ethyl, propyl, butyl, and the like, and polar radical derivatives thereof such as halogen and the like; dimethano octahydronaphthalene, an alkyl derivative thereof, an alkylidene derivative thereof, and a polar radical derivative such as halogen and the like, such as 6-methyl-1,4:5,8-dimetha-no-1,4,4a,5,6,7,8,8a-octahydronaphthalene, 6-ethyl-1,4:5,8-dimethano-1,4,4-a,5,6,7,8,8a-octahydronaphthalene, 6-ethylidene-1,4:5,8-dimethano-1,4,4a,5,-,6,7,8,8a-octahydronaphthalene, 6-chloro-1,4:5,8-dimethano-1,4,4a,5,6,7,8,-8a-octahydronaphthalene, 6-cyano-1,4:5,8-dimethano-1,4,4a,5,6,7,8,8a-octahydronaphthalene, 6-pyridyl-1,4:5,8-dimethano-1,4,4a,5,6,7,8,8a-octahydronaphthalene, 6-methoxycarbonyl-1,4:5,8-dimethano-1,4,4a,5,6,7,8,8a-octahydronaphthalene, and the like; and trimers and tetramers of cyclopentadiene such as 4,9:5,8-dimethano-3a,4,4a,5,8,8a,9,9a-octahydro-1H-benzoindene, 4,11:5,10:6,9-trimethano-3a,4,4a,5,5a,6,9,9a,10,10a,11,11a-dodecahydro 1H-cyclopentaanthracene, and the like.

Examples of poly (cyclic olefin) include the following:

(a) Saturated cycles produced by hydrogenating a ring-opening polymer via a normal hydrogenation method, the ring-opening polymer being produced by polymerizing the aforementioned monomers via standard ring-opening polymerization methods;

(b) Copolymers of any the aforementioned cyclic olefins and ethylene;

(c) Saturated cycles produced by hydrogenating homopolymers of monomers induced by 1,3-cyclopentadiene, 1,3-cyclohexadiene, 1,3-cycloheptadiene, 1,3-cyclooctadiene, and substituent derivatives thereof, and the like, and cyclohexadiene monomer polymers via a normal hydrogenation method, the cyclohexadiene monomer polymers being copolymers comprising the aforementioned monomers and other monomers such as chain conjugated diene monomer units induced by 1,3-butadiene, isoprene, 1,3-pentadiene, 1,3-hexadiene, and the like, and/or vinyl aromatic monomer units induced by styrene, α-methylstyrene, o-methylstyrene, p-methylstyrene, p-tert butylstyrene 1,3-dimethylstyrene, divinylbenzene, vinylnaphthalene, diphenylethylene, vinylpyridine, and the like; and (d) Saturated cycles gained by hydrogenating homopolymers of the aforementioned vinyl aromatic monomers and copolymers of vinyl aromatic monomers and polar vinyl monomer units via a normal hydrogenation method, the polar vinyl monomer units being induced by chain conjugated diene and/or methyl methacrylate, methyl acrylate, acrylonitrile, methyl vinyl ketone, α-methyl cyanoacrylate, and the like. One or two types or more of these cyclic olefin copolymers can be used via blending.

Moreover, other polymers can be combined with the cyclic polyolefin resin used in the present invention if required.

To protect the substrate from UV while treating with ozone, various options are available. Ozone oxidation can be performed under ambient light conditions if ambient UV light is negligible. Performing the treatment in the dark is also contemplated. This could be achieved for example by having a light proof reaction chamber or by having the treatment done in a dark room.

Ozone can be in the gas phase or in solution. In the gas phase, the concentration is typically greater than 0.1%, and preferably it is 3% by weight. In solution, although water is usually used as a solvent for the ozone solution, an organic or inorganic polar solvent can be used as the solvent for the ozone solution. The ozone treatment can typically be carried out for 30 seconds to 60 minutes. In the gas phase with the ozone at 3% by weight, a typical treatment time is 10 minutes. At lower ozone concentrations exposure time can be increased. Conversely, at higher ozone concentrations, exposure time can be decreased.

All fluorescence-based assays that are known using glass as a substrate can be performed using the ozone-treated poly (cyclic olefin) of the invention, including but not limited to, oligonucleotide probe detection, high throughput screening assays based on oligonucleotides, and immunoassays. Fluorescent dyes that are typically used in glass-based assays are also suitable for assays using a microdevice of the present invention. For example, Cy3™ and Cy5™ may be used.

EXAMPLES

All chemical reagents were purchased from Aldrich, except for 5-(and-6)-((N-(5-aminopentyl)amino)carbonyl) tetramethylrhodamine (also known as tetramethylrhodamine cadaverine) which was purchased from Molecular Probes and Cy3 and Cy5 which were purchased from Amersham. Oligomers of DNA were custom synthesized by the microarraying facilities at NRC's Biotechnology Research Institute (BRI). Zeonor™ and Zeonex™ resins were purchased from Zeon Chemicals. PMMA-VSUVT™, -HT121-825 were obtained from Atoglas. PMMA-OptixCA41™ was purchased from Plexiglas. Topas™ resins were obtained from Ticona.

Infrared spectra were collected with a Nicolet Magna™ 860 infrared spectrometer equipped with a single reflection ATR (Attenuated Total Reflectance) accessory with a germanium window. XPS spectra were collected with a PHI-5500™ XPS spectrometer from Physical Electronics operated with a monochromatic Al X-ray source at 300 W. Sample charging was minimized with an electron flood-gun which was adjusted accordingly to minimize line widths. In all cases, the C 1s aliphatic peak was set to 285 eV. Optical transmission spectra from 1 mm thick sheets of plastics were collected with a Beckman DU-640™ spectrometer. Fluorescence spectra from solid rectangular prisms (10×6×40 mm) for each plastic were acquired with a SPEX fluorolog2-F111AI™ using 1.25 mm fixed slits.

The rectanglular plastic prisms were fabricated by pressing the molten polymer in a polished aluminum block between two silicon wafers using an EVG hot embossing instrument. The wafers had been pretreated with octyltrichlorosilane which acts a mold releasing agent.

Ozone oxidation was accomplished in 10 minutes with an $O_3$zomax OZO-2VTT™ ozone generator that produced 3% by weight ozone. Plastic slides having the same dimensions as standard microscope slides were fabricated in the same manner as the rectangular prisms. Surface modification of Zeonor and Zeonex poly(cyclic olefin) slides was accomplished in a two-step process. The first step involved the surface oxidation with ozone for 10 minutes. Subsequently, the slides were treated with a freshly prepared solution of 8 mg 1-ethyl-3-(3-dimethylaminopropyl)carbodiimide (EDC) and 2 mg N-hydroxysuccinimide (NHS) in 100 μL of phosphate buffered saline (PBS, pH=7.4) solution for 1 hour.

Figure 7:
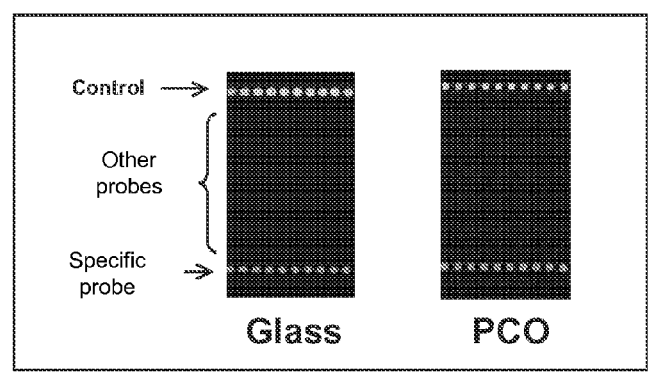
FIG. 7 shows the comparison of the performance of an ozone-treated poly(cyclic olefin) substrate of the invention and a conventional glass substrate in detection of fluorescently labelled amplicons.

Arraying of oligonucleotides on chemically modified poly (cyclic olefin) slides was accomplished by dispensing via capillary action a 6 μM solution of an amino-modified single stranded oligonucleotide (15mer) using a 1-10 μL eppendorf pipeter mounted on a XYZ micro translator from ThorLabs (MT3™) or by dispensing from a commercially available arrayer (Virtek SDDC-2™ from Bio-Rad Laboratories) (FIG. 7). The arrayed oligonucleotide solutions were allowed to react with plastic surfaces for 1 h in a humid chamber at 37° C. Unreacted oligonucleotide was removed by washing the slides with a solution of 0.1% sodium dodecyl sulphate (SDS) in PBS. Slides were further treated with a 1M solution of ethanolamine in PBS (pH=8.4) for 1 h.

Hybridization buffer consisted of a solution containing 6×SSPE buffer, 0.03% polyvinylpyrrolidone and 30% formamide. All hybridization experiments were carried out at room temperature using an equimolar mixture of the complementary and non-complementary strands at a concentration of 0.8 μM. A hybridization time of 1 h was allowed for all passive hybridizations. In order to remove non-specifically bound DNA, all microarrays were washed 3 times with 0.1% SDS in PBS for 5 min each time. Fluorescent images of the hybridized oligonucleotides were acquired with a ScanArray Lite-ALCST01™ from Perkin Elmer. Injection of solutions in the microfluidic experiments were carried out with a syringe pump from Kd Scientific Inc. (Kds210™) using a flow rate of 1.4 μL/min for an equimolar mixture of complementary (target#1) and non-complementary (target#2) DNA (0.8 μM, 10 μL) and 8.3 μL/min for the washing solution (0.1% sodium dodecyl in PBS, 50 μL). Microfluidic experiments have also been carried out using a CD platform similar to one described by Peytavi et. al. (Régis Peytavi, 1 Frédéric R. Raymond, 1 Dominic Gagné, 1 François J. Picard, Guangyao Jia, 2 Jim Zoval, 2 Marc Madou, 2 Karel Boissinot, 1 Maurice Boissinot, Luc Bissonnette, 1 Marc Ouellette, 1 and Michel G. Bergeron. Clinical Chemistry 51:10, (2005) 1836-1844).

Example 1

Selection of Substrate

The ideal substrate needed for the fabrication of high throughput screening devices that are based on fluorescence detection should have the following properties: i) provide rapid microfabricaton and scalable production that will ensure low-cost manufacturing, ii) low intrinsic fluorescence background as well as low fluorescence due to non-specific-binding and iii) allow a simple, scalable and environmentally friendly surface chemistry for the immobilization of biomolecules.

Substrates were pre-screened solely based on their performance in micromachining, namely hot embossing, optical transmission and intrinsic fluorescence. The microfabrication requirement can be met by restricting the potential substrates to thermoplastics since embossing is a suitable technique for industrial fabrication. Further refinement of the list of potential plastics was accomplished by excluding polymers containing aromatic or conjugated systems since they are expected to have a significant intrinsic fluorescence.

As a consequence, different commercial grades of poly (methylmethacrylate) (PMMA: VSUVT™, HT121™, V825™ and OptixCA41™) and a number of poly(cyclic olefins) available commercially under the trade names of Topas (5013™ and 8007™), Zeonor (480™, 750R™, 1020R™, 1060R™ and 1600™) and Zeonex E48R™ formed the initial set of potential polymeric resins.

Optical transmission curves were generated (not shown) for the substrates under consideration. As expected, the optical properties for any particular polymer are highly dependent on the commercial grade used. Defining 50% transmittance as the mininum acceptable transparency, PMMA-VSUVT had the widest transparency window for wavelengths as short as 275 nm. PMMA-V825 did not transmit in the UV region since it is not transparent below 365 nm. The other two grades of PMMA were the least transparent since they did not transmit efficiently below approximately 380 nm. The large variation in optical transparencies is most likely due the nature of additives such mold-releasing agents that are present in commercial resins.

From the poly(cyclic olefins) that were studied, Zeonor 480 and 750R had the highest transparencies in the UV-visible region since they transmit at wavelengths as short as 285 and 270 nm, respectively. All other poly(cyclic olefins) reach 50% transmittance at 295 nm.

All these substrates are optically transparent in the region between 400 and 700 nm. This transparency window is sufficiently wide for a large number of fluorophores, particularly the commonly used fluorescent dyes, Cy3 and Cy5, which have excitation wavelengths at 550 and 650 nm and emission wavelengths at 570 and 670 nm, respectively.

In addition to the optical transparencies, the bulk intrinsic fluorescence of the various possible substrates was examined (data not shown). Steady state fluorescence emission spectra from plastic rectangular prisms were acquired using excitation wavelengths at 543 and 633 nm, which correspond to the ones employed for the detection of Cy3 and Cy5 in Perkin Elmer biochip scanners.

The emission spectra obtained using an excitation wavelength of 543 nm and an emission wavelength of between 570 and 590 nm, as used for the detection of Cy3 indicated that Zeonor 480 had a strong fluorescent emission and therefore it is not a suitable substrate for the fabrication of devices that employ fluorescence detection in the Cy3 region. Secondly, three polymers, Topas 5013, PMMA-V825 and Zeonor 1600, had a higher intrinsic fluorescence when compared to other polymers. However, surface fluorescence measurements using a standard microarray scanner indicated that the background fluorescence from PMMA-V825 was acceptable since it is low compared to the signals observed with typical DNA microarrays. As a consequence, all these substrates, with the exception of Zeonor 480, would be suitable for fluorescence detection in the Cy3 region. Zeonor 1060R had the lowest fluorescent background in this region.

A second region of interest corresponds to that of Cy5 fluorophore since it is a standard fluorescent dye in DNA microarray technologies. Fluorescent spectra using an excitation wavelength of 633 nm were acquired in the same manner as before and the uncorrected spectra (data not shown). This excitation wavelength corresponds to the laser employed in Perkin Elmer biochip scanners. It was clear that PMMA-HT121, Topas 8007 and PMMA-V825 had the highest fluorescence emission in the region near 670-680 nm. In fact, surface fluorescence measurements (Table 1) using a Perkin Elmer biochip scanner indicated that the background fluorescence for PMMA-HT121 and -V825 were 127 and 45 times higher than the intrinsic fluorescence of glass, respectively. Based on this data, these two PMMA resins and Topas 8007 are not suitable substrates. In addition, PMMA-OptixCA41 had a fluorescence background that was 19 times higher than that of glass. Zeonor 1020R, Zeonor 480 had higher fluorescence backgrounds than PMMA-OptixCA41. As a consequence, PMMA-VSUVT, Zeonor 750R, Zeonor 1600, Topas 5013, Zeonex E48R and Zeonor 1060R are potential substrates for fluorescence detection in the Cy5 region. In this case, Zeonor 1060R had the lowest intrinsic fluorescence background.

TABLE 1

Relative background fluorescence from selected substrates.

| Substrate | Cy3 region | Cy5 region |
| --- | --- | --- |
| Glass | 1 ± 0.3 | 1 ± 0.3 |
| PMMA-VSUVT | 1.8 ± 0.5 | 2.8 ± 0.5 |
| PMMA-V825 | 3.9 ± 0.8 | 45 ± 4 |
| PMMA-HT121 | 2.2 ± 0.5 | 127 ± 5 |
| PMMA-OptixCA41 | 6 ± 1 | 19 ± 2 |
| Zeonor 1060R | 1.1 ± 0.5 | 1.8 ± 0.5 |
| Zeonex E48R | 1.4 ± 0.5 | 2.3 ± 0.5 |

Based on the optical properties above, PMMA-VSUVT and Zeonor 1060R have the most suitable intrinsic properties for fluorescence-based assays in the Cy3 and Cy5 fluorophore regions. It should be noted that fully integrated devices such as micro Total Analysis Systems (μTAS) based on fluorescence detection may be required to operate at temperatures close to the boiling point of water. For such situations, Zeonex E48R can be considered due to its excellent optical properties and its relatively high glass transition temperature (Tg=139° C.) as compared to PMMA-VSUVT (Tg=94° C.) or Zeonor 1060R (Tg=100° C.).

Example 2

Comparison of Poly(cyclic olefin) Intrinsic Fluorescence Levels

FIG. 1a shows the level of intrinsic fluorescence from a sample of Zeonor 1060R after treatment with 3% ozone in the absence of UV, with excitation at 550 nm and emission at 570 nm (Cy3 wavelengths). Similarly, FIG. 1c shows the level of fluorescence from a sample of Zeonor 1060R after treatment with 3% ozone in the absence of UV for 1 hour, with excitation at 650 nm and emission at 670 nm (Cy5 wavelengths). These figures can be contrasted with FIGS. 1b and 1d which show the levels of intrinsic fluorescence when a sample of Zeonor 1060R is treated with 3% ozone while irradiating with the full spectrum of a 100 Watts mercury lamp for 1 hour, at Cy3 and Cy5 wavelengths respectively.

Example 3

Surface Chemistry and Immobilization of DNA on Poly(Cyclic Olefins)

Generally poly(cyclic olefins) are obtained from the copolymerization of ethene and a cyclic olefin. For instance, Topas™ (Ticona Inc.) and APEL™ (Mitsui Chemical) are synthesized via chain copolymerization of monomers such as 8,9,10-trinorborn-2-ene (norbornene) or 1,2,3,3,4,4a,5,8,8a-octahydro-1,4:5,8-dimethanonaphthalene (tetracyclo dodecene) with ethene yielding a saturated hydrocarbon. On the other hand, Zeonex and Zeonor resins are produced by ring-opening metathesis polymerization of a number of cyclic olefinic monomers, followed by a hydrogenation step. The hydrogenation step is necessary for increasing the thermal stability of the plastic by removing carbon-carbon double bonds that are necessarily formed during the polymerization process (T. Nielsen, D. Nilsson, F. Bundgaard, P. Shi, P. Szabo, O. Geschke, A. Kristensen, J. Vac. Sci. Technol. B 2004, 22, 4, 1770-1775; J. Y. Shin, J. Y. Park, C. Liu, J. He, Pure Appl. Chem. 2005, 77, 5, 801-814; F. Bundgaard, T. Nielsen, D. Nilsson, P. Shi, G. Perozziello, A. Kristensen, O. Geschke, Micro Total Analysis Systems 2004, 2, 297, 372-374).

Although there exist poly(cyclic olefins) that contain ethers, esters and aromatic groups, a number of commercial poly(cyclic olefins) are saturated hydrocarbons. Consequently, it is difficult to introduce suitable functional groups at the surface of these chemically innert plastics which are expected to have a low intrinsic fluoresence background.

It is known from previous literature reports that ozone oxidation of other plastics generates hydroxyl groups, esters, ketones and carboxylic acids (M. R. Davidson, S. A. Mitchell, R. H. Bradley, Surface Science 2005, 581, 2-3, 169-177; H. C. Beachell, S. P. Nemphos, J. Polym. Sci. 1956, 21, 113-124; G. D. Cooper, M. Prober, J. Polym. Sci. 1960, 44, 397-409). Although the mechanism for the oxidation process is not known with certainty, some studies indicate that hydroperoxides and peroxyl radicals are involved (J. Yamauchi, A. Yamaoka, K. Ikemoto, T. Matsui, Bull. Chem. Soc. Jpn. 1991, 64, 1173-1177). However, there is considerable evidence for the formation of hydrotrioxides which have been observed at low temperatures and which are formed via a direct insertion of ozone in a C—H bond (D. H. Giamalva, D. F. Church, W. A. Pryor, J. Org. Chem. 1988, 53, 15, 3429-3432). These reactive intermediates are the precursors for the formation alcohols and carbonyl-containing species.

The rapid oxidation of poly(cyclic olefins) with ozone in the presence and absence of UV light is shown in FIG. 2. Examination of the infrared spectrum of Zeonex E48R (FIG. 2) indicates that a broad band that corresponds to the OH stretch is observed in the region between 3600 and 2100 $cm^{-1}$. with a maximum at 3400 $cm^{-1}$. Such a broad OH stretch band is characteristic of carboxylic acids. However, the maximum at 3400 $cm^{-1}$ does indicate that alcohols are also contributing to this broad signal. This is in agreement with the literature since the formation of alcohols and carboxylic acids during ozonation has been reported for other polymeric systems (M. R. Davidson, S. A. Mitchell, R. H. Bradley, Surface Science 2005, 581, 2-3, 169-177; G. D. Cooper, M. Prober, J. Polym. Sci. 1960, 44, 397-409).

The second most significant feature of the infrared spectrum is the appearance of a strong signal at 1708 $cm^{-1}$ that corresponds to a C=O stretch from species with carbonyl or carboxyl groups. It is very likely that this signal is due to ketones, carboxylic acids and esters. Typically, unconjugated ketones appear at 1715 $cm^{-1}$ (cyclohexanone). However, the resonance frequency of ketones does vary significantly depending on the chemical environment. This can either increase or lower the frequency of ketones. In fact, non-polar solvents tend to increase the frequency, whereas polar solvents have the opposite effect. However, the overall change in frequency does not exceed 25 $cm^{-1}$ (R. M. Silverstein, F. X. Webster Spectrometric identification of organic compounds; sixth edition ed.; John Wiley & Sons, Inc., New York, 1998). Since the oxidation process of poly(cyclic olefins) produces highly polar surfaces, it is expected that the ketones which are formed will have their resonance frequencies lowered by the polar environment. The formation of ketones has been reported previously for the ozone oxidation of other polymeric systems (M. R. Davidson, S. A. Mitchell, R. H. Bradley, Surface Science 2005, 581, 2-3, 169-177). It should also be pointed out that it has been shown conclusively in the literature that the ozonation of norbornane in solution yields the corresponding ketone as a major product (D. H. Giamalva, D. F. Church, W. A. Pryor, J. Org. Chem. 1988, 53, 15, 3429-3432).

In addition to ketones, the infrared band at 1708 $cm^{-1}$ may also be due to carboxylic acids and esters. In fact, a visual inspection of this infrared band, suggests that several overlapping signals are present and closer examination indicates that a strong overlapping signal which is approximagely ⅔ of the overall band is present at 1730 $cm^{-1}$. This second overlapping band may be due to the presence of carboxylic acids and esters. In fact, the typical resonance frequency of unconjugated carboxylic acids is expected in the range of 1706-1720 $cm^{-1}$ for neat samples where the acids form dimers through hydrogen bonding. The resonance frequency for an isolated carboxylic acid (monomer) in the absence of hydrogen bonding is usually observed at 1760 $cm^{-1}$. Since XPS studies indicate that ozone treatment leads to a high concentration of protic groups, it is quite likely that the generated carboxylic acids will exhibit a resonance frequency near 1730 $cm^{-1}$ as a result of extensive hydrogen bonding.

The formation of esters has been reported during ozone oxidation of other plastics (M. R. Davidson, S. A. Mitchell, R. H. Bradley, Surface Science 2005, 581, 2-3, 169-177). Esters typically appear in the range between 1735 and 1750 $cm^{-1}$. However, their presence cannot be confirmed or ruled out based on the present data. A rather weak and broad signal at 1630 $cm^{-1}$ is also observed to overlapp with the 1708 $cm^{-1}$ band. It is very likely that this band might be due to the formation of carbon-carbon double bonds. Indeed, the formation of double bonds has been reported during the oxidation of polypropylene (L. F. Macmanus, M. J. Walzak, N. S. Mcintyre, J. Polym. Sci. A 1999, 37, 2489-2501).

The presence of ethers cannot be confirmed or ruled out with the present data since their expected C—O stretch in the region of 1150-1085 is obscured by a broad signal that extends from 1430 to 700 $cm^{-1}$. The broad signal might be due to significant overlap of infrared bands from chemically different ketones, carboxylic acids, etc.

On the other hand, UV-ozone oxidation is a much more aggressive treatment since ozone is directly photolyzed with UV light at 254 nm to give oxygen and oxygen atoms. This is readily observed in the infrared spectrum of Zeonex E48R (FIG. 2) after oxidation with UV-ozone. In this situation, much more intense infrared bands are observed for the OH stretch in the region of 3600 and 2100 $cm^{-1}$ and the C=O (carbonyl) stretch at 1716 $cm^{-1}$. It should be noted that the position of the carbonyl signal increases by 8 $cm^{-1}$ compared to the corresponding signal that is obtained from the sample that was oxidized in the absence of UV light. The shift can be attributed to the formation of a higher proportion of carboxylic acids and perhaps esters.

Besides the bands related to the OH and C=O stretch, a new broad band is observed at 1180 cm$^{-1}$ during the photolysis of ozone. This band may arise from the formation of peroxides. In fact, formation of peroxides has been reported during the oxidation of other plastics (L. F. Macmanus, M. J. Walzak, N. S. Mcintyre, J. Polym. Sci. A 1999, 37, 2489-2501; A. A. Kefely, S. K. Rakovski, D. M. Shopov, S. D. Razumovskii, R. S. Rakovski, G. E. Zaikov, J. Polym. Sci. A 1981, 19, 2175-2184).

In addition to infrared spectroscopy, X-ray Photoelectron Spectroscopy (XPS) was employed for the characterization of the oxidation process in Zeonex E48R. The XPS spectrum from a pristine sample of Zeonex E48R contained essentially a single peak at 285.0 eV which corresponds to the C 1s and it is characteristic of a saturated hydrocarbon, as expected. NMR studies also corroborate that Zeonex E48R is saturated hydrocarbon. Line deconvolution of the single peak at 285.0 eV indicates that there is a very small peak at 285.8 eV which is most likely due to a vibrational component that is normally observed in aliphatic polymers. Small peaks were also observed for 0 is, Si 2s and Si 2p and they are highly consistent with traces of silicon dioxide from the silicon mold employed in the fabrication of the plastic slides.

Figure 3:
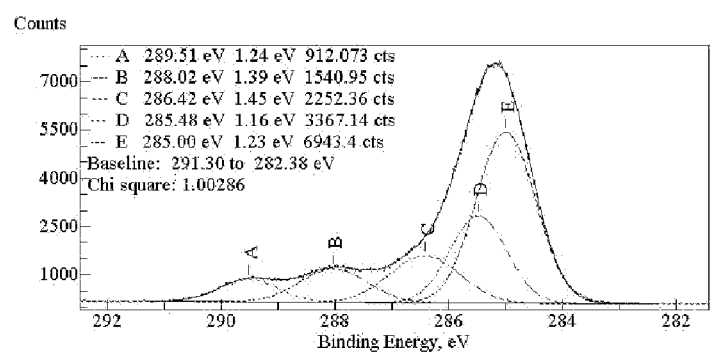
FIG. 3 shows the convoluted and deconvoluted XPS spectra of the ozone oxidation of a poly(cyclic olefin) in the absence of UV light after 1 hour.

The survey XPS spectrum of the oxidized Zeonex E48R indicated that a high degree of oxidation had occurred since 28% of atomic oxygen is present on the sample. This indicates that the degree of oxidation at the surface, strictly speaking, should be significantly higher since XPS samples a depth of approximately 5 nm. One would expect that the degree of oxidation should decrease with depth due to limited diffusion of ozone into the polymeric matrix. Line deconvolution of the C is peak in the high resolution spectrum was found to contain 5 lines (FIG. 3). Results from line deconvolution are presented in Table 2.

TABLE 2

Line deconvolution of C 1s from oxidized Zeonex E48R.

| Peak | BE (eV) | FWHM (eV) | Area % |
|------|---------|-----------|--------|
| A    | 289.51  | 1.24      | 6.1%   |
| B    | 288.02  | 1.39      | 10.3%  |
| C    | 286.42  | 1.45      | 15.0%  |
| D    | 285.48  | 1.16      | 22.4%  |
| E    | 285.00  | 1.23      | 46.2%  |

Peak A at 289.5 eV is typical of carboxylic carbons in carboxylic acids or esters. When combined with the infrared data, it provides strong evidence for the existence of carboxylic acid groups on the surface of polycyclic olefins after ozone oxidation (G. Beamson, D. Briggs High resolution XPS of organic polymers; John Wiley & Sons: New York, 1992). Peak B at 288.0 eV is indicative of carbons that are double bonded to oxygen (C=O) or bonded to two different oxygen atoms (O—C—O) (G. Beamson, D. Briggs High resolution XPS of organic polymers; John Wiley & Sons: New York, 1992). This is consistent with the reported formation of ketones. However the existence of the formation of acetals in small concentrations cannot be discarded.

It turns out that if one were to consider the number of oxygen atoms that are expected to be present based on the relative populations of the carbons that are directly bonded to oxygen (ensuring that the carbon atoms are not counted twice), a C=O group is highly consistent with O:C ratio that is obtained from the survey spectrum. Peak C at 286.4 eV is consistent with carbon atoms bonded to one oxygen atom (C—O) as for the case of ethers and alcohols (G. Beamson, D. Briggs High resolution XPS of organic polymers; John Wiley & Sons: New York, 1992). Formation of alcohols is consistent with the infrared data. However, it is very likely that ethers are also formed. Peak D at 285.5 eV is associated with carbon atoms that are not directly bonded to oxygen (C*-C=O) and to carbon atoms linked to ester groups (C(=O)—O—C*). The major peak E at 285.0 eV is due to the unoxidized aliphatic carbons (G. Beamson, D. Briggs High resolution XPS of organic polymers; John Wiley & Sons: New York, 1992).

Further evidence for the presence of carboxylic acids was obtained from the expected chemical reactivity of these groups. 1,6-Diaminohexane was reacted with the oxidized surface of Zeonex E48R in the presence of EDC and NHS. Detection of the amino groups at the surface was accomplished with fluorescamine. This fluorescent dye ($\lambda_{exc}$=380 nm and $\lambda_{em}$=464 nm) is particularly useful for the detection of amino groups since it is a non-fluorescent compound that becomes highly fluorescent upon reaction with primary amines. A control experiment was carried out in the same manner without the ozone oxidation. No fluorescence could be observed on the control experiment.

Figure 4:
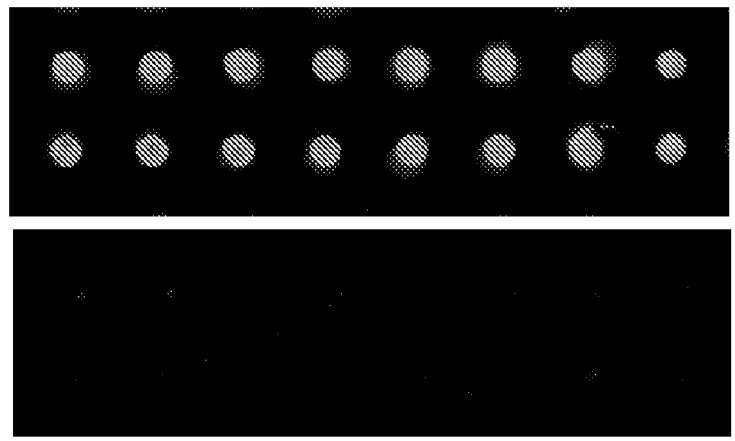
FIG. 4 shows fluorescence measurements indicating the presence of chemically immobilized tetramethyl rhodamine cadaverine on the surface of ozone-oxidized poly(cyclic olefin) (top) and the corresponding control experiment performed in the absence of ozone oxidation (bottom).

In order to demonstrate the feasibility of these chemically modified surfaces for the immobilization of molecules in an array format, plastic slides of Zeonor 1060R and Zeonex E48R were oxidized with ozone in the absence of UV for 1 h. The slides were subsequently treated with EDC and NHS as described previously in order to generate the corresponding NHS ester at the surface of the plastics. A 4 μM solution of tetramethylrhodamine cadaverine ($\lambda_{exc}$=544 nm, $\lambda_{em}$=571 nm) was arrayed on surface. This fluorescent dye has not only a primary amino group which reacts readily with NHS esters but also it fluoresces in the same region as Cy3. Fluorescent images of the array on Zeonor 1060R, along with the control experiment, are illustrated in FIG. 4. Similar images were obtained for Zeonex E48R. It should be noted that the slides were thoroughly washed and sonicated with 0.1% SDS in PBS to ensure that only the chemically bound material is retained.

Figure 5:
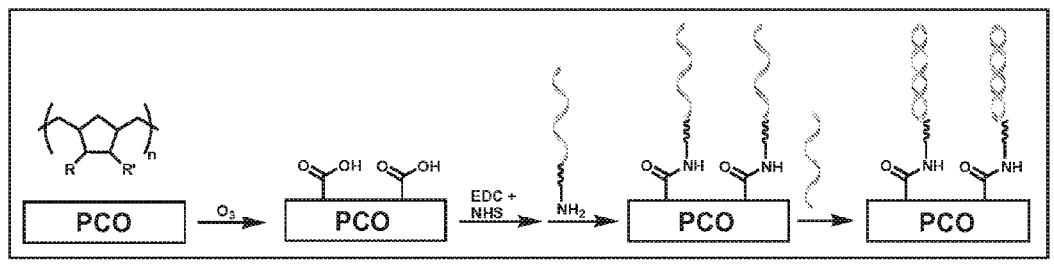
FIG. 5 is a schematic illustrating the ozone-treatment of a poly(cyclic olefin) followed by covalent binding of reagents at the newly created carboxylic acid groups.
Figure 6:
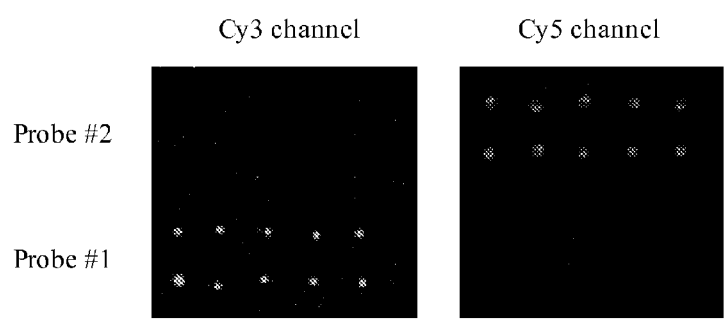
FIG. 6 shows a hybridization assay using different Cy3- and Cy5-labelled targets and their complementary probes bound to the slide. The assay was performed under competative binding conditions.

One general strategy for the covalent attachment of DNA on poly(cyclic olefins) is illustrated in FIG. 5 and this is achieved in the same manner as for the fluorescent dye. Poly (cyclic olefin) slides of Zeonor 1060R and Zeonex E48R were oxidized and subsequently modified as the corresponding NHS ester. Two amino-modified single strands of DNA (probe#1 and probe#2) were arrayed and allowed to react with the surface (Table 3). The immobilized oligonucleotides were hybridized in a competitive manner with an equimolar mixture of their respective complementary strands (target#1-Cy3 and target#2-Cy5). Molecular recognition is observed as illustrated by the fluorescent images of the hybridized oligonucleotide arrays on Zeonor 1060R which are presented in FIG. 6. Similar results are observed for DNA oligonucleotide on Zeonex E48R (data not shown).

FIG. 7 shows that the sensitivity of an assay performed on a poly(cyclic olefin) substrate is comparable to the same assay performed on glass. The assay conditions were the same in each case. The fluorescence intensity in the "control" and "specific probe" rows is comparable across each row, as is the absence of fluorescent signal from the "other probes" region of each slide. In this case, the hybridization was carried out with amplicons.

TABLE 3

DNA oligonucleotide sequences and their respective modifications

| Name | Sequence | Modification |
| --- | --- | --- |
| Probe#1 | 5'-CCGCTCGCCAGCTCC-3' | 5'-(CH$_2$CH$_2$O)$_6$-NH$_2$ |
| Probe#2 | 5'-ATTATGAGTGTCCTA-3' | 5'-(CH$_2$CH$_2$O)$_6$-NH$_2$ |
| Target#1 | 5'-GGAGCTGGCGAGCGG-3' | 5'-Cy3 |
| Target#2 | 5'-TAGGACACTCATAAT-3' | 5'-Cy5 |

What is claimed is:

1. A method of making a microdevice for the immobilization of biomolecules for the purpose of carrying out a fluorescence-based assay, said method comprising:
   providing a substrate comprising a poly(cyclic olefin);
   protecting the substrate from ultraviolet (UV) light; and
   subjecting a surface of said UV-protected substrate to ozone oxidation to activate said surface;
wherein a content of intrinsic fluorophores on the surface of the substrate remains substantially unchanged after the ozone oxidation.

2. A method according to claim 1, further comprising covalently reacting at least part of the activated surface with a reagent for the immobilization of biomolecules on the surface.

3. A method according to claim 2, wherein the reagent is reacted with carboxylic acid groups on the activated surface.

4. A method according to claim 3, wherein the reagent produces amine groups on the surface.

5. A method according to claim 3, wherein the reagent is N-hydroxysuccinimide.

6. A method according to claim 4, wherein the reagent is 1,6-diaminohexane.

7. A method according to claim 3, wherein the reagent produces aldehyde groups on the surface.

8. A method according to claim 7, wherein the reagent is:
   (a) 1,6-diaminohexane;
   (b) gluteraldehyde; and
   (c) sodium cyanoborohydride (NaCNBH$_3$).

9. A method according to claim 1, wherein the ozone is in the gas phase.

10. A method according to claim 9, wherein the ozone is at a concentration of 3% by weight.

11. A method according to claim 9, wherein the ozone oxidation is carried out for 30 seconds to 60 minutes.

12. A method according to claim 11, wherein the ozone oxidation is carried out for 10 minutes.

13. A method according to claim 1, wherein the poly(cyclic olefin) comprises saturated hydrocarbon side groups.

14. A method according to claim 13, wherein the hydrocarbon side groups are alicyclic side groups.

15. A method according to claim 14, wherein the alicyclic side groups are cycloalkanes having 4 to 30 carbon atoms.

* * * * *